United States Patent [19]
McClelland et al.

[11] Patent Number: 5,070,242
[45] Date of Patent: Dec. 3, 1991

[54] APPARATUS AND METHOD FOR TRANSIENT THERMAL INFRARED SPECTROMETRY

[75] Inventors: John F. McClelland; Roger W. Jones, both of Ames, Iowa

[73] Assignee: Iowa State University Research Foundation, Inc., Ames, Iowa

[21] Appl. No.: 546,738

[22] Filed: Jul. 2, 1990

Related U.S. Application Data

[63] Continuation-in-part of Ser. No. 576,448, Sep. 12, 1990, which is a continuation-in-part of Ser. No. 415,714, Oct. 21, 1989, which is a continuation-in-part of Ser. No. 297,297, Jan. 13, 1989, abandoned.

[51] Int. Cl.$^5$ .............................................. G01N 21/71
[52] U.S. Cl. ...................................... 250/339; 250/340
[58] Field of Search ................... 250/340, 339; 374/5; 356/311

[56] References Cited

U.S. PATENT DOCUMENTS

| | | | |
|---|---|---|---|
| 4,716,293 | 12/1987 | Harrick | 250/340 |
| 4,791,299 | 12/1988 | Naito et al. | 250/352 |
| 4,823,009 | 4/1989 | Biemann et al. | 250/341 |
| 4,886,370 | 12/1989 | Koshihara et al. | 374/5 |
| 4,982,089 | 1/1991 | Johnson | 250/304 |

FOREIGN PATENT DOCUMENTS 58-124938  7/1983  Japan .................................... 374/5

Primary Examiner—Constantine Hannaher
Attorney, Agent, or Firm—Antonelli, Terry, Stout & Kraus

[57] ABSTRACT

A method and apparatus for enabling analysis of a material (16, 42) by applying a cooling medium (20, 54) to cool a thin surface layer portion of the material and to transiently generate a temperature differential between the thin surface layer portion and the lower portion of the material sufficient to alter the thermal infrared emission spectrum of the material from the black-body thermal infrared emission spectrum of the material. The altered thermal infrared emission spectrum of the material is detected by a spectrometer/detector (28, 50) while the altered thermal infrared emission spectrum is sufficiently free of self-absorption by the material of the emitted infrared radiation. The detection is effected prior to the temperature differential propagating into the lower portion of the material to an extent such that the altered thermal infrared emission spectrum is no longer sufficiently free of self-absorption by the material of emitted infrared radiation, so that the detected altered thermal infrared emission spectrum is indicative of the characteristics relating to the molecular composition of the material.

21 Claims, 7 Drawing Sheets

APPARATUS AND METHOD FOR TRANSIENT THERMAL INFRARED SPECTROMETRY

CROSS REFERENCE TO RELATED APPLICATIONS

This application is a Continuation-In-Part of copending application No. PCT/US90/00122, filed Jan. 12, 1990 now U.S. Application Ser. No. 576,448, filed Sept. 12, 1990, which is a Continuation-In-Part of Application Ser. No. 415,714, filed Oct. 2, 1989, now abandoned, which is a Continuation-in-Part of U.S. Application Ser. No. 297,297, filed Jan. 13, 1989, now abandoned, the disclosures of the aforementioned applications being incorporated by reference herein.

DESCRIPTION

1. Technical Field

The present invention relates to spectroscopic analysis of materials, and particularly, to non-contact, remote spectroscopic analysis of a quantity of moving or stationary material based on transient thermal infrared emission from the material.

2. Background Art

There are numerous types of analytical methods which currently are known for deriving information about materials. Spectroscopy is a well known and general method for analyzing materials. There are a number of types of spectroscopic methods which, in turn, are applicable to certain types of analyses and measurements, and which have advantages and disadvantages.

Presently, there is a need for improvements in the ability to analyze materials, especially in those cases where such analyses need to be quick, efficient, and accurate. Additionally, there is a real need for such analyses for "in-process" situations; that is, directly on-line with respect to the manufacturing or the processing of materials.

For many materials, there are a variety of generally conventional spectroscopic methods for analyzing the content and other characteristics of the materials. Some of those methods are infrared transmission, diffuse reflectance, photoacoustic, and emission spectroscopies While generally these methods give satisfactory results, they are deficient because they require selective, and often destructive, sampling of the materials. Some materials (coal, for example) require grinding or pulverizing. The material must often be removed to a remote laboratory location where the testing and equipment requires time and resources to provide the results. Currently, other than as described in the aforementioned applications, no contemporaneous, non-destructive, on-line infrared analysis is reasonably possible for solid materials inclusive of semisolid materials such as flexible or rubber-like materials.

Many of the aforementioned presently used methods also lack much flexibility in their use. While some of the methods do not require destructive sampling such as grinding or pulverizing, they may not be operable for materials of greater than minimal thickness, or for materials of varying thickness. Conventional transmission, reflection, or emission spectroscopies have problems because the optical density of many materials is too high to permit accurate and reliable measurement. That is, upon heating of a sample, such sample strongly reabsorbs the same wavelengths it strongly thermally emits as infrared radiation When a thick sample is heated, the deep layers of the sample emit strongly at the preferred wavelengths and only weakly at other wavelengths. This deep-layer strong emission at preferred wavelengths, however, is greatly attenuated before leaving the sample since surface layers of the thick sample preferentially absorb those particular wavelengths and such process is termed "self-absorption". Self-absorption in optically-thick samples causes severe truncation of strong spectroscopic bands and leads to emission spectra which closely resemble black-body emission spectra representative of an optically thick material being heated to a uniform temperature and which contain little spectral structure characteristic of the material being analyzed.

Attempts have been made to solve this self-absorption problem by thinning sample materials. High-quality spectra of free-standing films and thin layers on low-emission substrates are routinely measured. However, this requires selective sampling and processing of the materials being analyzed For other types of spectroscopic methods such as photoacoustic spectrometry which are less subject to optical density problems, deficiencies exist in that they are not easily performed on moving streams of materials. Thus, there is a real need in the art for an apparatus and method which has the flexibility to be used both for moving and stationary materials; and for materials which may have significant optical densities and which are heat sensitive.

There is a further need for an apparatus and method which does not require the use of additive materials to or processing of the sample materials, and which can analyze non-destructively and remotely. For example, in some spectroscopic methods, the materials must be ground to fine powders and then diluted in a transparent matrix. Of course, any destructive processing or additive procedures would alter the beginning state of the material being analyzed. For an analytical apparatus and method to be used effectively in a production line, any fundamental change in the material must be avoided. For example, if variable-in-size crushed coal were being analyzed on a moving conveyor, no grinding or addition of any substance would be allowed, as the coal could not then be utilized for its intended purpose in its original state.

DISCLOSURE OF THE INVENTION

It is therefore a principal object of the present invention to improve upon or overcome the deficiencies and problems in the art.

Another object of the present invention is to provide an apparatus and method of thermal transient infrared transmission spectroscopy which can be utilized on either moving or stationary materials, and which does not require application of heat to the material so as to be utilizable for heat sensitive materials Another object of the present invention is to provide an apparatus and method for analyzing a solid material inclusive of a semisolid material such as a flexible or rubber-like material, or a liquid material such as a molten material which is to be extruded, by transiently generating a temperature differential between a thin surface layer portion and a lower portion sufficient to alter the thermal infrared emission spectrum from the black-body thermal emission spectrum of the material by cooling the thin surface layer portion and detecting the altered thermal emission spectrum of the material while the altered thermal emission spectrum is sufficiently free of self-absorption by the material of emitted infrared radiation.

Another object to the present invention is to provide an apparatus and method as above described which can be accomplished generally without physical contact with the material.

A further object to the present invention is to provide an apparatus and method as above described which can be done remotely from the material being analyzed.

A further object to the present invention is to provide an apparatus and method as above described which can derive the molecular composition of a material, and various physical and chemical properties of the material that are related to molecular composition.

Another object to the present invention is to provide an apparatus and method as above described which can be utilized directly on production or processing lines which handle the materials.

A still further object to the present invention is to provide an apparatus and method as above described which is non-destructive to the material being analyzed.

A further object to the present invention is to provide an apparatus and method as above described which can also be utilized to analyze either large or small samples of the materials in laboratory settings A still further object to the present invention is to provide an apparatus and method as above described which can be utilized with optically dense materials.

A further object to the present invention is to provide an apparatus and method as above described which overcomes the spectroscopic problems caused by self-absorption of the emitted radiation from the material being analyzed, A further object of the present invention is to provide an apparatus and method as above described which can be utilized for stationary materials, or for an unknown quantity of moving material, on both a continuous and non-destructive basis.

Another object of the present invention is to provide an apparatus and method as above described which can be directly utilized in-process for an unknown quantity of moving material A further object of the present invention is to provide an apparatus and method as above described which is economical, efficient and reliable.

Another object of the present invention is to provide an apparatus and method as above described which can operate within the extreme and changing conditions of a processing environment for materials, or within a laboratory setting A further object of the invention is to provide an apparatus and method as above described, which can be combined with a computer system to derive information about the materials useful for processing, control, and understanding of the material.

The present invention provides an apparatus and method for nondestructively analyzing either stationary or moving materials, particularly solid materials inclusive of semisolid materials which are flexible or rubber-like or liquid material such as molten materials which are to be extruded, by infrared spectroscopy A temperature differential is transiently generated between a thin surface layer portion of the material and a lower portion of the material sufficient to alter the thermal infrared emission spectrum of the material from the black-body thermal infrared emission spectrum of the material. That is, by cooling a part of the surface of the material, a transient temperature differential is generated between the thin surface layer portion and lower portion of the material sufficient to alter the thermal infrared emission spectrum of the material from the black-body thermal infrared emission spectrum thereof. Since this temperature differential propagates to the lower portion of the material, the altered thermal infrared emission spectrum of the material is detected while the altered thermal infrared emission spectrum is sufficiently free of self-absorption by the material of emitted infrared radiation, prior to the temperature differential propagating into the lower portion of the material to an extent such that the altered thermal infrared emission spectrum is no longer sufficiently free of self-absorption by the material of emitted infrared radiation. The altered thermal infrared emission spectrum is detected as an infrared spectrum by a spectrometer, for example, and the spectrum contains information on the molecular composition of the material. Thereafter, characteristics relating to the molecular composition of the material may be determined based upon the detected altered thermal infrared emission.

In accordance with the present invention, a cooling source imposes, for example, a cooling jet to a part of the surface of the material to cause transient cooling of the thin surface layer of the material and superpositioning of the transmission spectrum of the cooled layer on the emission of infrared radiation from the hotter lower portion of material below the cooled layer resulting in the altered infrared emission which is detected. Because the bulk of the material, i.e., all of the material below the cooled or chilled layer having a depth l, is at a uniform temperature, the bulk or lower portion of the material will emit a black-body spectrum characteristic of the temperature $T_H$. If the chilled surface layer is optically thin so that $l < 1/\beta$, where $\beta$ is the absorption coefficient, then the surface layer will emit a negligible amount of infrared as compared to the amount passing through it from the bulk, both because it is thin and because emission intensity is proportional to $T^4$, so that the cooled the surface layer will absorb infrared from the bulk emission and altered thermal infrared emission will be detected Thus, the cooled or chilled layer will behave in the manner of a sample of thickness l when placed in an infrared spectrometer whose source is at temperature $T_H$ and the emission reaching the spectrometer will be a transmission spectrum of the optically thin cooled layer and will be referred to hereinafter as a "transmission spectrum"

In accordance with the present invention, the cooling of the surface of the material may be effected by a jet of cold gas or some other cold source for rapidly cooling the surface of the material within the field of view of a spectrometer. The material may be a solid or liquid and may be a moving stream of material or may be stationary. The application of a jet of cold gas, for example, produces an optically thin, chilled layer at the surface of the material within the field of view of the spectrometer and the layer thickens and warms by thermal diffusion in which the temperature differential between the thin surface layer portion and the lower portion of the material propagates into the lower portion of the material. The spectrometer may be controlled to effect detection only when the chilled layer within the spectrometer field of view remains thin or there may be effected relative movement of the material with respect to the field of view of the spectrometer so that as the layer thickens and warms by thermal diffusion, it is carried out of the field of view of the spectrometer by such relative motion. Since the chilled surface layer starts to thicken immediately after being formed, i.e., the temperature differential propagates into the lower portion of the material, the longer the chilled layer is observed by the spectrometer after its formation, the greater the average observed thickness of the layer will be, and the higher the observed optical density of the layer will be. The faster that the material is moved through the spectrometer field of view, either by reducing the size of the field of view or by increasing the speed of the observed material, the less the amount of saturation which is caused by self-absorption.

In accordance with the present invention, the analysis and detection of the transmission spectrum or altered thermal infrared emission is accomplished by a spectrometer and detector which, in preferred embodiments, can be, for example, a cooled HgCdTe infrared detector The detector operates so as to detect the altered thermal infrared emission spectrum of the material which has been altered from the black-body thermal infrared emission spectrum of the material as a result of the generation of the temperature differential transiently in the thin surface layer portion by cooling of such thin surface layer portion while the altered thermal infrared emission spectrum is sufficiently free of self-absorption by the material of emitted infrared radiation, prior to the temperature differential propagating through the lower portion of the material to an extent such that the altered thermal infrared emission spectrum is no longer sufficiently free of self-absorption by the material of emitted infrared radiation, so that the detected altered thermal infrared emission spectrum is indicative of characteristics relating to the molecular composition of the material. Such detection may be achieved in the case of a pulsed cooling jet applied to a stationary material by controlling the operation of the detector in accordance with the application of a cooling jet so that the detector is activated for a predetermined period to achieve the detection as described. Alternatively, if continuous cooling is applied to the surface of a material and the material is moving, the field of the detector is set in relation to movement of the material so that substantially only the altered thermal emission spectrum which is substantially free of self-absorption appears within the field of view of the detector as a result of movement of the material. Control arrangements may also be provided so as to able to detect the transmission spectrum or altered thermal infrared emission spectrum which is substantially free of self-absorption by suitable detection of the detected spectrum. That is, by suitable filtering of the detected wavelengths.

In accordance with the present invention, the detector may be controlled by a control arrangement and/or provide an output to a control arrangement including a processor having appropriate software for deriving different characteristics from the detected and selected spectra of the infrared radiation from the material. Additionally, such control arrangement or processor may include appropriate computer memory, storage, and printer or graphic components.

The invention can be utilized as a non-contact, remote analytical apparatus and method for measuring infrared absorbance spectra of materials, either in a moving stream or in a stationary setting. The cooling of the thin, near surface layer of the material can be accomplished by either pulsing a cooling jet in time onto the material, or moving the material relative to the applied cooling, or both. The transmission spectrum or altered thermal infrared emission spectrum from the material is analyzed by the detector to obtain infrared absorbance spectra of the material. The infrared absorbance spectra are then used to determine molecular composition and other correlated properties.

The invention therefore provides efficient and accurate emission spectroscopic analysis of materials without requiring heating thereof and is particularly useful in heat sensitive materials or molten materials. It eliminates the selective sampling, grinding or other preparation required by presently utilized systems.

The invention can also be adapted to a variety of situations. It can be utilized in laboratory settings for a variety of different types and sizes of materials, and it can be utilized on-line in production settings. By utilizing computer software and hardware, it can form an integral part of process control by 0 being able to derive this information during processing, without contact or sampling, or destruction of material being processed. It can also be used to assist in controlling how the processing of the material proceeds.

These and other objects, features and advantages of the present invention will become more apparent with reference to the accompanying drawings

BEST MODE FOR CARRYING OUT THE INVENTION

Figure 1:
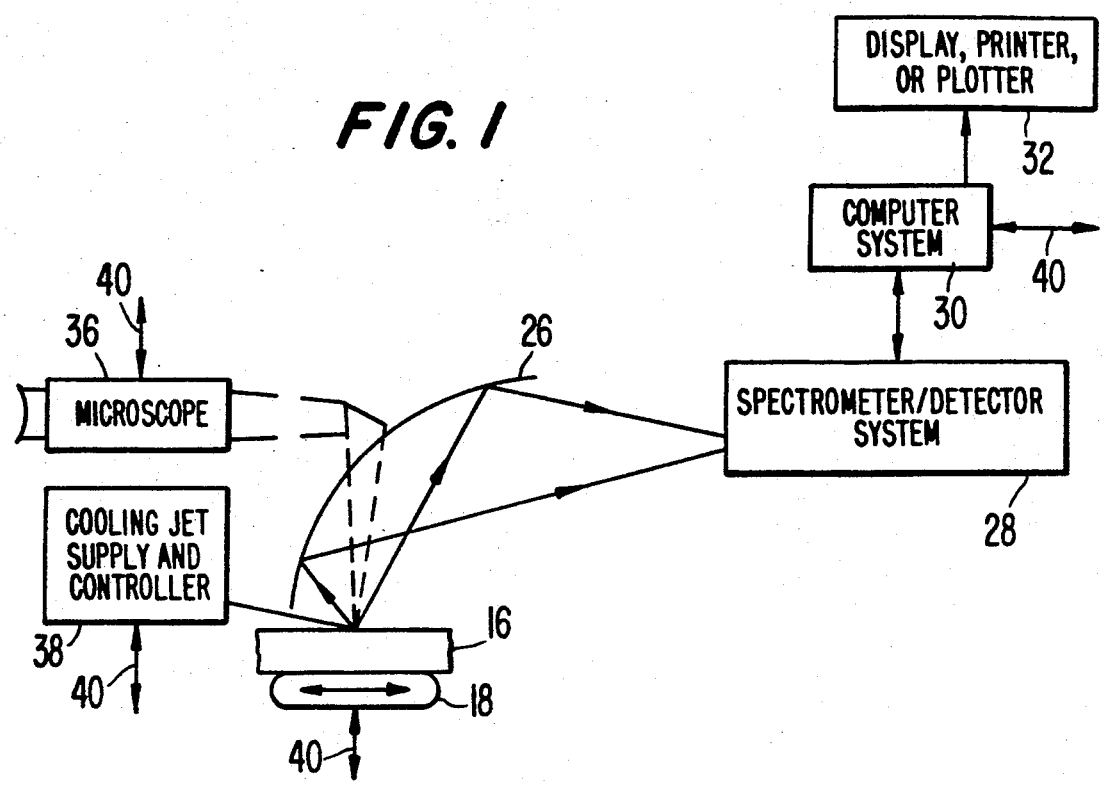
FIG. 1 is a block diagram arrangement of an embodiment of the present invention.

With respect to the drawings, a detailed description of the preferred embodiments of the invention will now be described wherein FIG. 1 illustrates an embodiment of the invention which can be utilized to analyze either stationary or moving material. Referring to FIG. 1, the sample or material 6 to be analyzed is disposed, for example, on a material position controller 18 such as a material transporter, for example, a conveyor, rotary table or a positioning table which can be controlled to accurately position the sample material 16. The type of sample position controller 18 depends upon the selected operation. A cooling jet supply and controller 20 is provided which can be operated either in a pulsed or continuous mode and a cooling jet is directed onto the material 16 Collection optics 26, such as are known in the art, are used to focus the infrared radiation emitted by the sample material 16 onto spectrometer/detector system 28, which system generates an electrical signal as a function of wave number of the emitted radiation. A computer system 30 is also provided which controls the spectrometer/detector system 28 as well as controllers 18 and 20 and processes the spectrometer/detector system 28 signals in order to obtain the chemical or physical information required from the analysis. The computer system 30 also control measurement components, display results and commands auxiliary systems. An output from the computer system may also be supplied to a display, printer or plotter 32. In the illustrated embodiment of FIG. 1, there is shown a microscope system 36 having appropriate optics for viewing the analysis area on the sample material 16, that is, the area of intersection of the cooling jet onto the material 16.

Reference numeral 40 designates communication connections or links between the computer system 30 and other components and controls of the embodiment. Computer system 30 can therefore, by appropriate software, operate the cooling jet supply and control 20, sample position controller 18, spectrometer/detector system 28 and microscope system 36. Other components and controls can also optionally be operated by the computer system 30, as desired.

The embodiment of FIG. 1 is flexible and adaptable to be used for different materials, and different analytical procedures. This embodiment can analyze moving or stationary materials and the composition of the cooling jet upon the material 16 causes transient cooling in a thin surface layer of the material 16 by pulsing the cooling jet over time, or by rapid relative motion between the cooling jet and the material 16, or by a combination of both. The application of the cooling jet generates a temperature differential between the cooled thin surface layer portion of the material and a lower portion of the material sufficient to alter the thermal infrared emission spectrum of the material from the black-body thermal infrared emission spectrum of the material. The altered thermal infrared emission spectrum of the material representative of the transmission spectrum as described above is detected while such altered thermal infrared emission spectrum is sufficiently free of self-absorption by the material of emitted infrared radiation, prior to the temperature differential propagating into the lower portion of the material to an extent such that the altered thermal infrared emission spectrum is no longer sufficiently free of self-absorption by the material of emitted infrared radiation, so that the detected altered thermal infrared emission spectrum is indicative of characteristics relating to the molecular composition of the material. The emitted radiation is detected and measured by the spectrometer/detector system 28 and the computer system 30 then processes the signal to obtain molecular concentrations or other physical or chemical information through correlation techniques as required by any number of different operations, such as process control, quality control, analytical chemistry, or nondestructive evaluation applications including ratioing or the like. The quantitative analysis may be effected utilizing commercial principle-component-regression (PCR) software (CIRCOM from Perkin-Elmer).

The spectrometer/detector system 28 may be any suitable type of spectrophotometer such as a Perkin-Elmer 1800 spectrophotometer having a wide-band liquid-nitrogen-cooled HgCdTe detector. Furthermore, the computer system 30 can include appropriate computers utilizing software and complementary data for deriving different material characteristics from infrared emission spectra. Additionally, such system can utilize appropriate software, displays, complementary data and servosystems for enabling decision making and for transmitting and executing commands based on the infrared spectra.

In FIG. 1, the sample material 16 to be analyzed is moved on a conveyor belt 18 or may be attached to a rotating disk, for example, and the cooling jet provided by the cooling jet supply and controller 20 is directed onto the surface of the sample material whereby the relative motion between the sample material and the impingement of the cooling jet on the surface of the material which is sweeping past the impingement point of the cooling jet effects transient cooling in a thin surface layer of the sample material. Radiation emitted by the sample material is focused by the collection optics 26 on the infrared spectrometer detector system 28. System 28 and the computer system 0 measures the emitted radiation intensity as a function of wavenumber in terms of an electrical signal with the computer system 30 providing an output to peripherals (display printer, and/or plotter 32) to display and record the data. The computer system 30 processes the infrared data to determine various material properties. The computer system 30 uses communication or command links 40 to control various components of the measurement system, for example, the cooling jet supply and controller 20, and to control other systems, such as processing equipment (not shown) based upon material properties determined by the on-line measurements.

The embodiment of FIG. 1 can also be used on a stationary sample material 16 which stationary measurement mode is appropriate for use in analytical laboratories where a moving stream of material 16 is not present. In this case, the cooling jet supply and controller 20 is pulsed with a pulse time which is short on the scale of a pulse repetition time Furthermore, a heating jet may be utilized to prevent the long term cooling in the sample material 16 and thereby return the sample material to its previous temperature. The microscope viewing system 36 can be employed to position the impingement spot of the cooling jet at a precise location on the sample 16 which enables microanalysis. In other regards, the stationary sample measurement mode is similar to the moving sample embodiment described above.

In the case of a pulsed cooling jet and a stationary or rotating sample material 16, due to the pulsed nature of the altered transient thermal emission from the material produced by the application of the cooling jet, it is preferable to synchronize the cooling jet supply with the spectrometer/detector system 28 sampling under control of the computer system 30. In this manner, the detection by the spectrometer/detector system is gated in accordance with the application of the cooling pulse to detect the transient altered thermal emission of infrared radiation from the material for a short time period, thereby avoiding detection of emissions effected by self-absorption. Other techniques may also be utilized and the spectrometer/detector may be provided with suitable filters.

Figure 2:
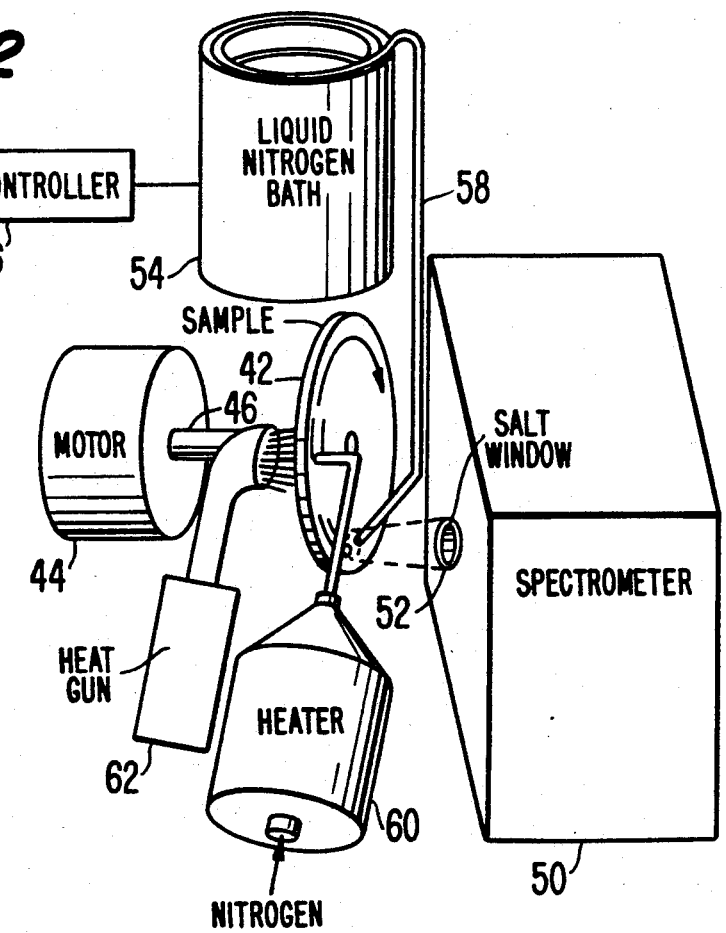
FIG. 2 is a schematic perspective view of a further embodiment of the present invention.

FIG. 2 shows another embodiment of the present invention for a better understanding of the invention and this embodiment was used to generate the spectra illustrated in FIGS. 3-6. With regard to the spectra of FIGS. 3 and 6, it should be noted that the illustrated curves showing the transmission spectra, on the scale, used do not show clearly the variation, especially in the high wavenumbers as, for example, wavenumbers 2000-4000 of curve C in FIG. 6. However, such variations do exist and are clearly shown in the resultant transmittance curve D of FIG. 6.

Referring to FIG. 2, solid sample material to be analyzed in the form of a rotating disk 42 is secured to a variable speed motor 44 through an axle 46 for spinning the disk 42. The normal infrared source of a Perkin-Elmer 1800 spectrophotometer was removed and the disk of the sample material 42 was positioned so that the spectrophotometer 50 viewed the sample normal to the surface thereof. The sample disk was mounted on the shaft 46 of the variable speed motor 44 and spun to simulate a continuous flow of fresh material through the spectrometer field of view. A salt (KCl) window 52 covered the spectrometer port without any other optics being utilized. The spectrometer had a wide-band liquid-nitrogen-cooled HgCdTe detector ($D^* = 1 \times 10^{10}$ cmHz$^{\frac{1}{2}}$ W$^{-2}$), operated at a 1.50 cm/s optical-path-difference velocity and 8cm$^{-1}$ nominal resolutions, and accumulated 256 scans for each spectrum.

The cooling jet supply was in the form of helium being chilled by passage through a liquid nitrogen bath 54 at 0.10 to 0.14 L/s. The stream of cold helium was directed onto the surface of the sample material disk 42 within the spectrometer field of view by a 1 mm inner-diameter tube 58 under control of a controller 56. The end of the tube 58 was positioned within 2 mm of the sample surface and was positioned at a 45° angle with respect to both the sample surface and the direction of motion of the sample to the field of view which is indicated by the arrow direction. Downstream from the field of view, a jet of heated nitrogen flowing from a heater 60 was directed onto the cooled or chilled surface track left by the cold jet. The temperature and flow rate of the nitrogen were adjusted so that the nitrogen raised the temperature of the surface of the sample material disk 42 to approximately the temperature value thereof prior to application of the cold jet. In this manner, the rotating sample disc 42 mimics a continuous flow of uniform-temperature material into the spectrometer field of view having a cold jet 22 applied thereto. For experimental purposes or in a laboratory environment, in order to raise the temperature of the sample material 42 above room temperature, a heat gun 62 was directed onto the rear of the sample disk 42 in order to raise the bulk sample temperature above room temperature, if desired.

Figure 3:
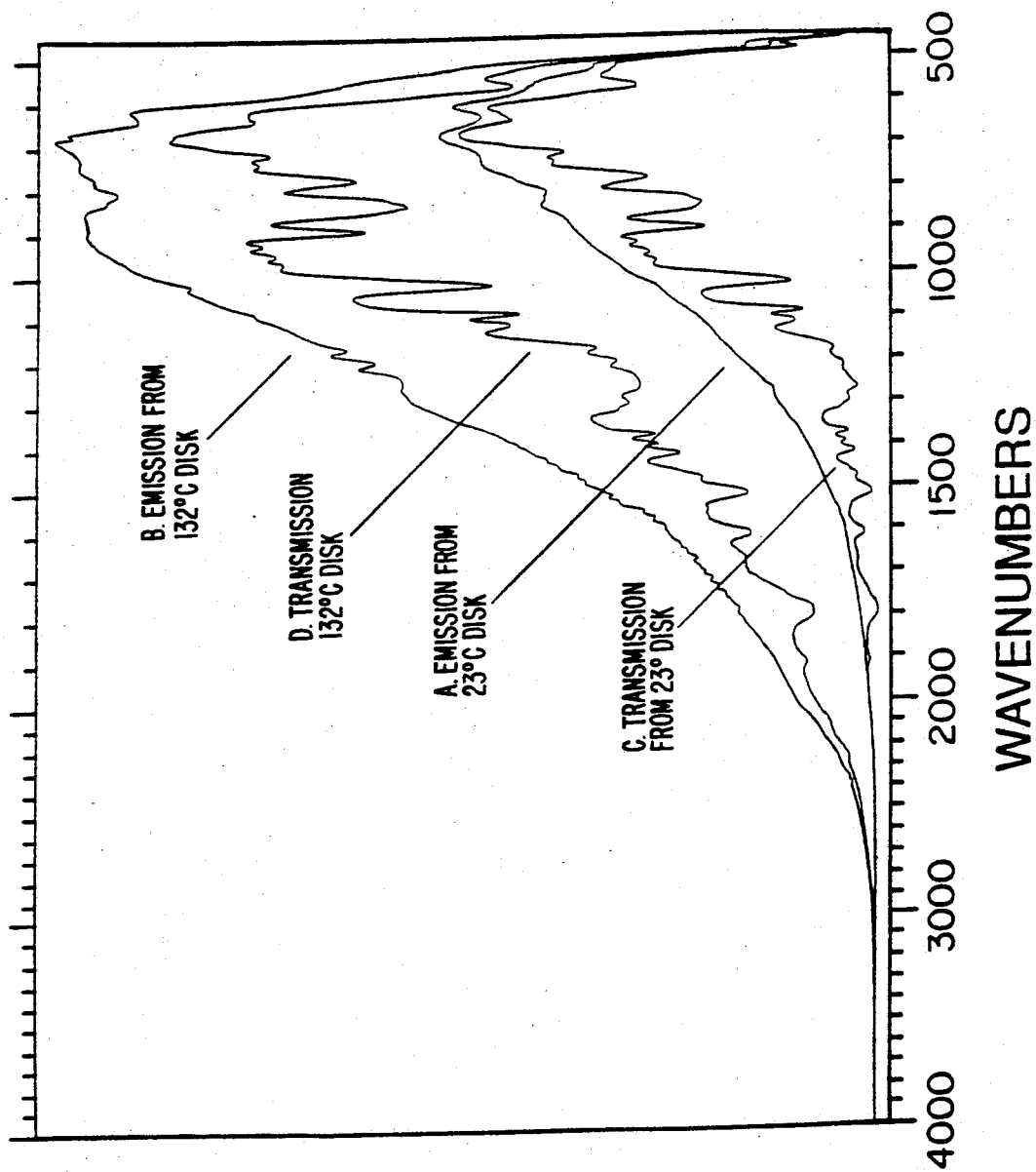
FIG. 3 is a graphical depiction of observed emissivity spectra for a 3 mm thick polycarbonate which is moving at 40.8 cm/s with respect to the detector for both a uniform sample temperature emission and with a cooled surface layer transmission at different temperatures.
Figure 5:
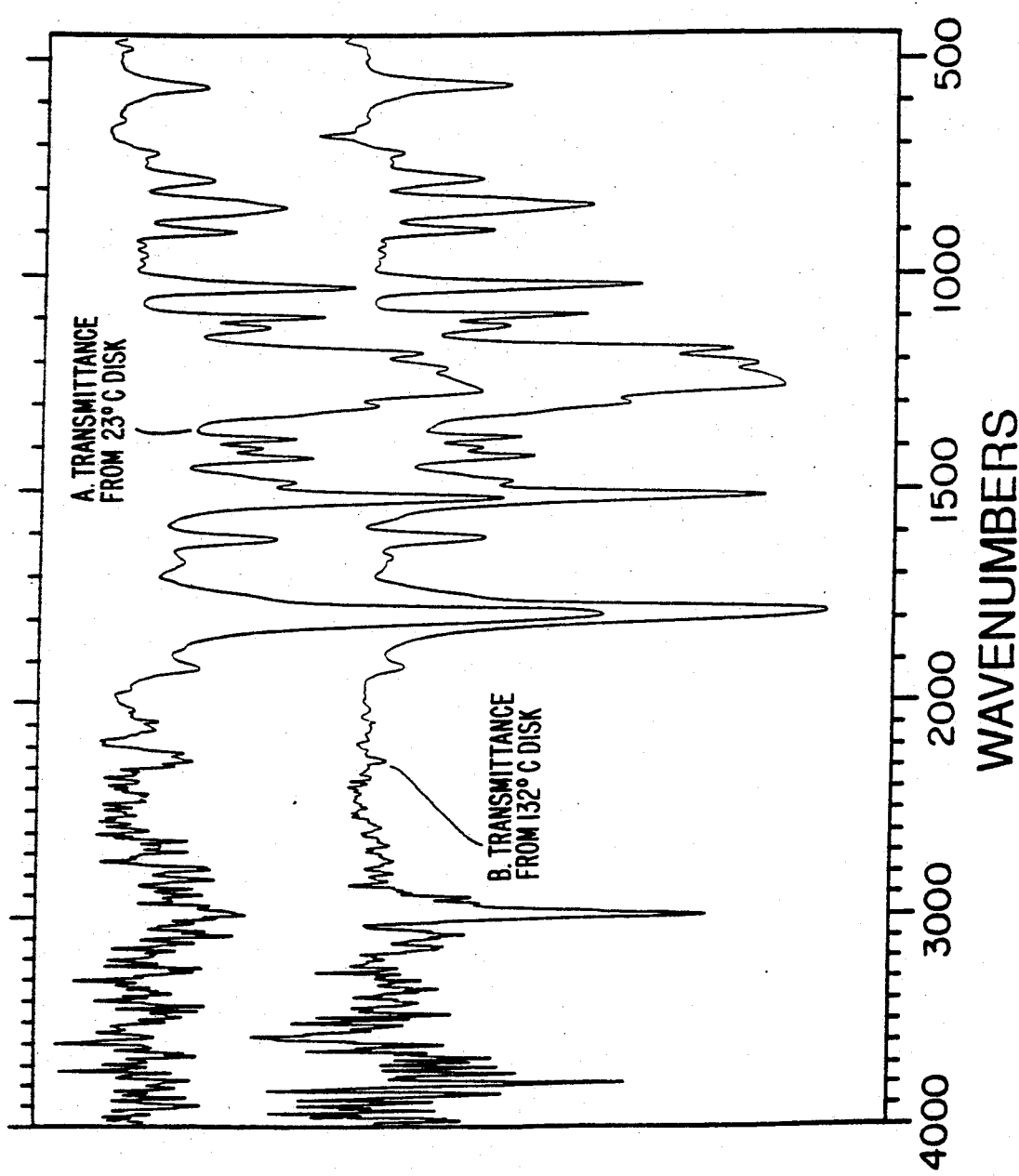
FIG. 5 is similar to FIG. 4 and wherein the 3 mm thick polycarbonate moved at a speed ten times faster than that of FIG. 3, i.e., at 408 cm/s.
Figure 6:
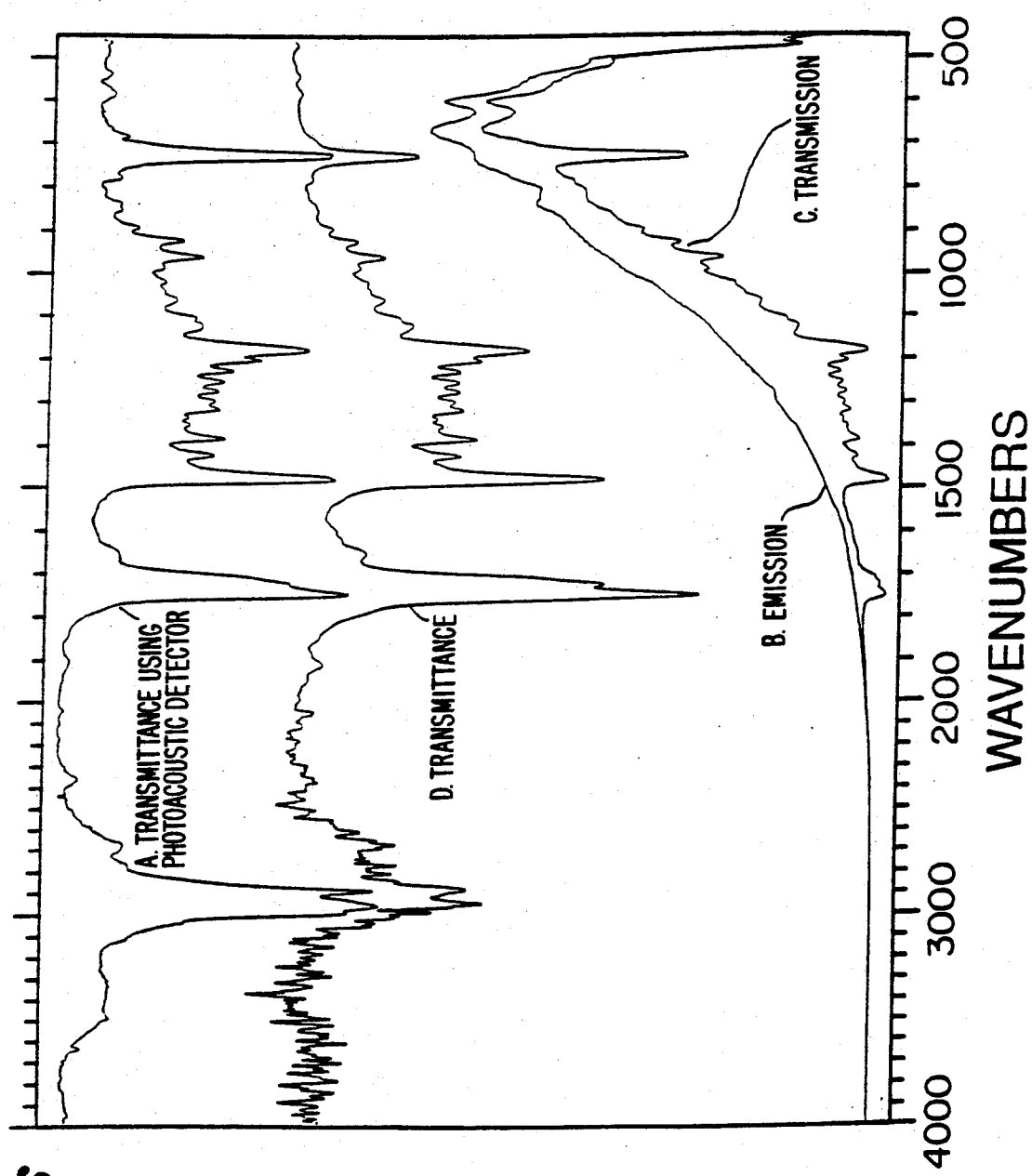
FIG. 6 is a graphical depiction of observed emissivity spectra for beeswax moving at 40.8 cm/s with respect to the detection for both a uniform sample temperature (emission), and a cooled surface layer (transmission), and by ratioing the emission and transmission spectra (transmittance), with a transmittance spectrum recorded photoacoustically being included for reference.

Conventional transmission spectra must be converted into transmittance spectra by ratioing with respect to a standard in order to compensate for the response function of the spectrometer and the emission curve of the infrared source. Accordingly, for the transmission spectra obtained in accordance with the present invention, the black-body emission curves observed from the rotating samples before the cold and hot jets are applied to the samples serve as the standards. These emission curves for polycarbonate and beeswax are shown in FIGS. 3 and 6. It is noted that noise produced zero and negative values in the weak, high-wavenumber tails of the standard emission and transmission spectra and to avoid division by zero and negative numbers, a small constant was added to the spectra for ratioing which type of processing is conventional. Further, other types of processing can be utilized including 9-point Savitzky-Golay smoothing for making the spectra illustrated in FIGS. 4-6 clearer at high wavenumbers.

Quantitative analysis was effected using the commercial principal-component-regression (PCR) software from Perkin-Elmer and it is noted that the data manipulation described above are not necessary for PCR analysis. However, prior to PCR analysis, the transmission spectra obtained in accordance with the present invention were scaled to a constant total intensity and then converted to transmittance-like spectra by ratioing with respect to a room-temperature black-body spectrum from carbon black, which carbon black spectrum was utilized to avoid introducing variations from ratioing each transmittance spectrum with respect to its own standard emission spectrum.

Figure 4:
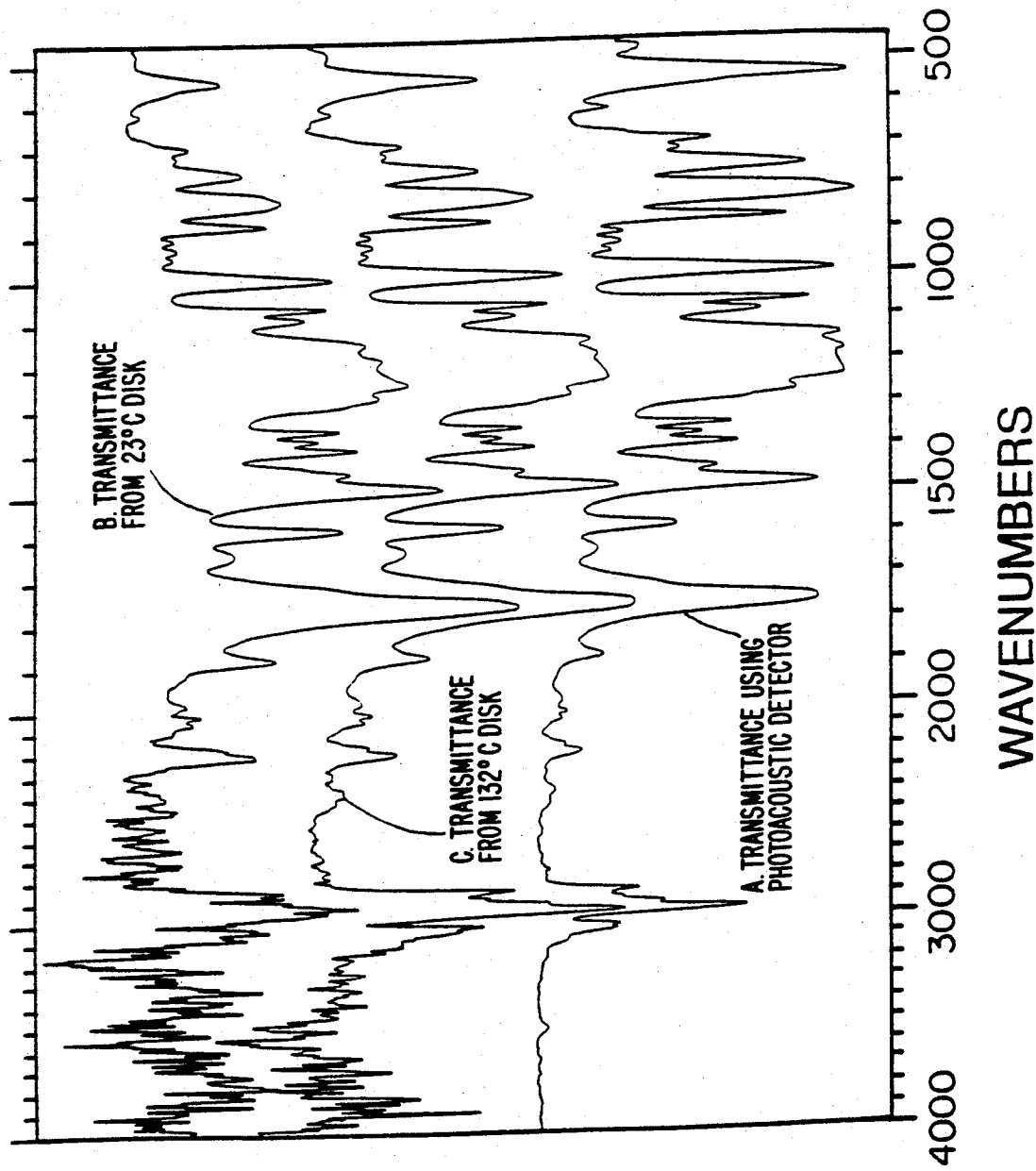
FIG. 4 is a graphical depiction of the spectra of FIG. 3 obtained by ratioing or dividing the spectra at the cooled surface layer transmission and the uniform sample temperature emission to obtain a transmittance spectrum as well as showing a reference transmittance spectrum recorded photoacoustically.

FIGS. 4 and 6 show curves (A) representing reference transmittance spectra which were not recorded by conventional transmission since the samples were optically thick. Instead, absorbance spectra were mounted in the spectrophotometer with its normal infrared source, and the absorbance spectra were converted mathematically to transmittance spectra. The absorbance spectra were recorded at 0.05 cm/s optical-path-difference velocity and 8 cm$^{-1}$ nominal resolution by accumulating 32 scans.

FIG. 3 shows both emission and transmission spectra for 3 a mm-thick polycarbonate (Lexan) travelling at 40.8 cm/s through the spectrometer field of view, which spectra have not been corrected for the response function of the spectrometer and detector Two emission curves (A and B) were recorded with the sample at a uniform temperature of 23° C. (curve A) and 132° C. (curve B) so that the emission curves represent black-body emission. The 23° C. emission spectrum (curve A) is virtually identical to that of a black-body emission spectrum whereas the 132° C. spectrum (curve B) has some structure characteristic of polycarbonate, but again is considered representative of a black-body emission spectrum. When the cold jet of FIG. 2 is applied, however, the observed emission changes drastically as the transmission spectrum of the thin, cold layer is superimposed on the emission providing the altered thermal infrared emission spectrum or transmission spectrum in accordance with the present invention as described above. The transmission spectra in accordance with the present invention have all of the characteristic features of polycarbonate with curve C representing the transmission spectra for the 23° C. temperature and curve D the transmission spectrum for the 132° C. temperature. The emission and transmission spectrum for curves A and C and curves B and D, respectively, were ratioed to produce the transmittance spectra curves B and C, respectively, as shown in FIG. 4.

The spectra in FIG. 4 for both transmittance obtained in accordance with the present invention and photoacoustically detected transmittance suffer from saturation which can be reduced by increasing sample speed or reducing the spectrometer field of view so that the average thickness of the cooled layer within the field of view is reduced. FIG. 5 shows transmittance spectra of the sample polycarbonate disk at the temperatures of 23° C. (curve A) and 132° C. (curve B) based upon ratioing with the emission spectra at such uniform temperatures, but at a 408 cm/s sample velocity representing 10 times the speed utilized in accordance with FIGS. 3 and 4. The spectra in FIG. 5 displayed less saturation than those in FIG. 4, including the reference photoacoustic spectrum. At the higher sample speed, the cooled layer is both thinner and not as cold so that the strength of absorption is reduced. Accordingly, the higher speed spectra have smaller signal-to-noise ratios.

Since the transient infrared transmission spectroscopy in accordance with the present invention works by reducing the surface temperature, an important advantage is that it can be applied and utilized with heat-sensitive materials. As an example, FIG. 6 shows spectra for yellow beeswax (Fisher Scientific) which melts at 62° C. to 65° C. and which is optically a highly scattering material. The beeswax was formed as a disk of an average 3 mm thickness at room temperature, as the sample 42 in FIG. 2 and rotated at a speed of 40.8 cm/s through the spectrometer field of view. The transmittance spectrum using a photoacoustic detector is shown in curve A with the emission spectrum for the sample material at 23° C. being shown in curve B and the transmission spectra in accordance with the present invention being shown in curve C. The transmittance spectrum (curve D) was derived by ratioing the emission and transmission spectra (curves B and C).

Figure 7:
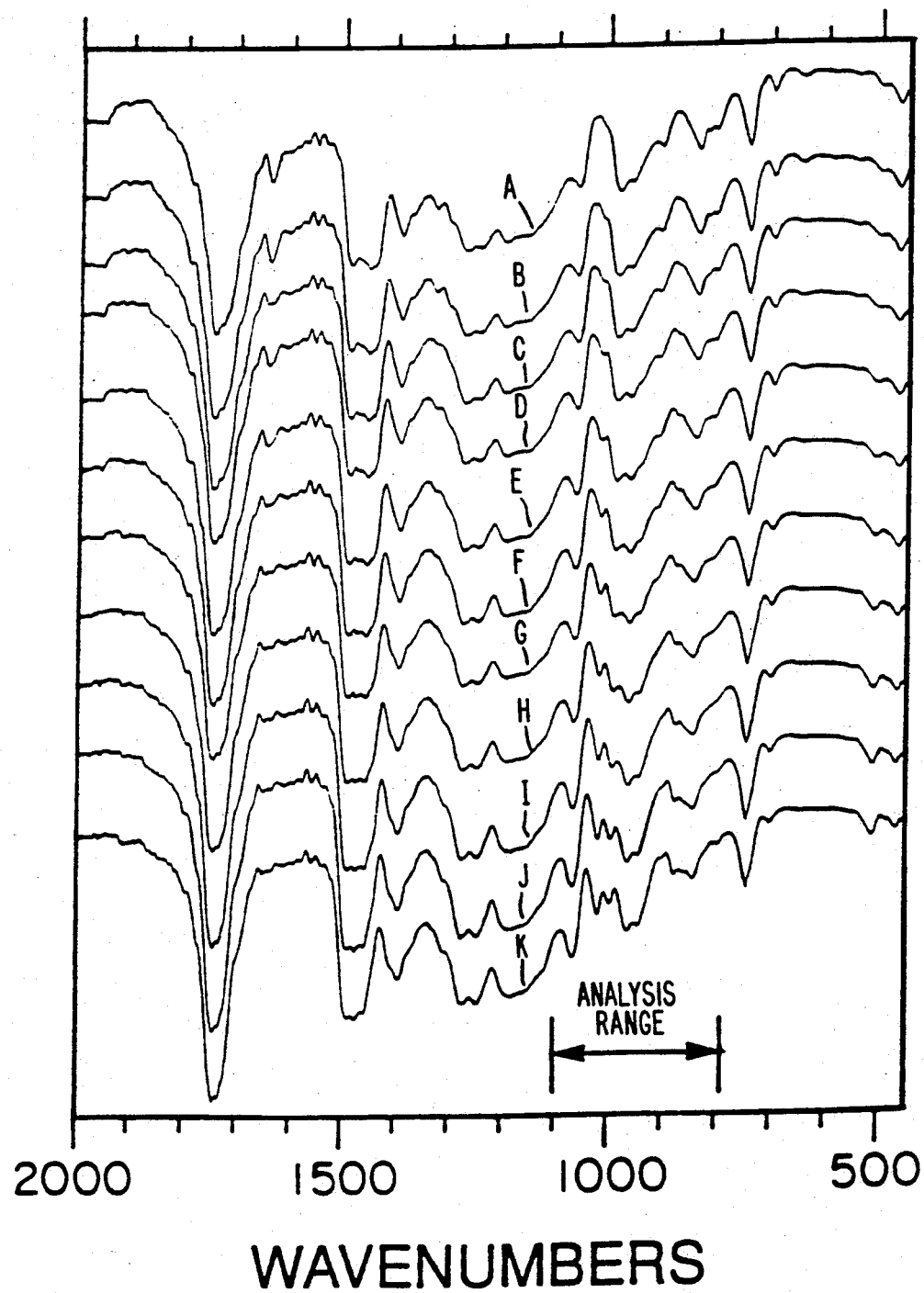
FIG. 7 is a graphical depiction of transmittance spectra of 40.8 cm/s, 3-mm-thick poly[(methyl methacrylate)-co-(butyl methacrylate)] composition materials with a 23° C. bulk temperature wherein compositions (a-k) are (top to bottom) 100.0, 93.1, 5.7, 77.8, 69.2, 60.0, 50.0, 39.1, 27.3, 14.3, and 0.0 mole percent methyl methacrylate.
Figure 8:
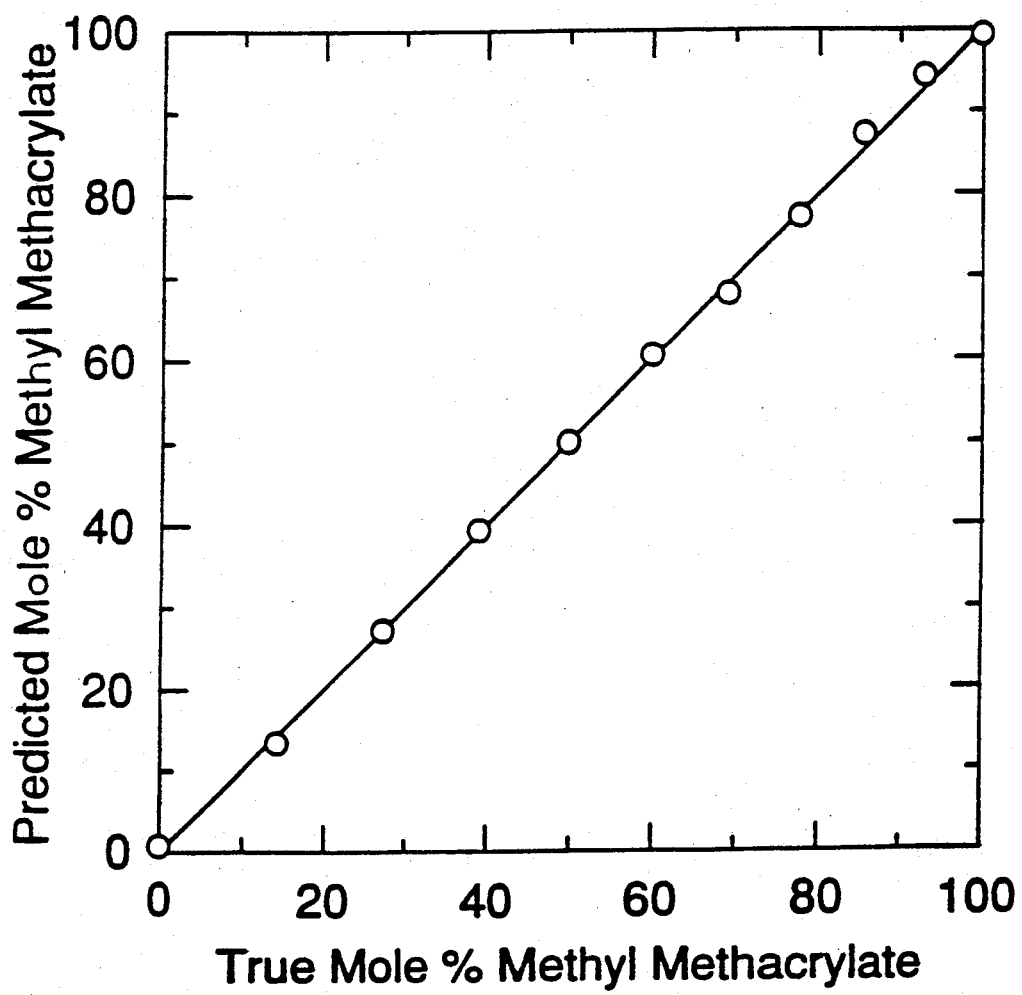
FIG. 8 is a graph showing compositions of copolymers of methyl and butyl methacrylate predicted by cross validating principal component regressions of 1100 to 790 $cm^{-1}$ region of the spectra in FIG. 7 plotted against the known sample compositions.

To show the quantitative ability of the present invention, the spectra of eleven copolymers of methyl methacrylate and n-butyl methacrylate were recorded utilizing the embodiment of FIG. 2 and analyzed by principal component regression (PCR). The sample disks averaged 3 mm in thickness and had compositions of 0.0, 14.3, 27.3, 39.1, 50.0, 60.0, 69.2, 77.8, 85.7, 93.1, and 100.0 mole percent methyl methacrylate. The transmission spectra were recorded with the disks at room temperature (23° C.) and moving at 40.8 cm/s. The transmittance spectra are shown in FIG. 7 in order of composition with pure poly(methyl methacrylate) at the top, i.e., 100.0 mole percent methyl methacrylate (curve A) and pure poly(butyl methacrylate), i.e., 0.0 percent methyl methacrylate (curve K) at the bottom. The spectra have obvious composition-dependent features, but there is extensive overlap of the methyl-related and butyl-related bands. A PCR cross validation was carried out using only the 1100 to 790 cm$^{-1}$ range of the spectra. In the cross-validation, each of the samples was chosen in turn as the unknown, the other ten samples acted as standards to calibrate the regression, and then the regression was used to predict the composition of the unknown. The eleven predicted compositions are plotted in FIG. 8 against the true compositions known from the synthesis of the samples. The standard error of prediction, which is the root-mean-square deviation of the predicted values from the true values is only 0.87 mole percent.

As apparent from the above description, the present invention produces quantitatively accurate spectra from optically thick, moving materials. Quantitative analysis is possible even at the low thermal-emission intensities from room temperature samples wherein a dynamic thermal gradient is induced so that the spectroscopic behavior of an optically thin layer of material differs from that of the rest of the sample. The present invention overcomes the problem of high optical density in solids that previously prevented the real-time infrared analysis of most solid samples and is insensitive to the reflectance and optical-scattering properties of samples while functioning in real time without sample preparation and does not involve raising sample temperature, so it can be applied where elevated temperatures cannot be used.

While we have shown and described several embodiments in accordance with the present invention, it is understood that the same is not limited thereto but is susceptible of numerous changes and modifications as known to those skilled in the art and we therefore do not wish to be limited to the details shown and described herein but intend to cover all such changes and modifications as are encompassed by the scope of the appended claims.

We claim:

1. A method for enabling analysis of a material comprising the steps of:
   cooling a thin surface layer portion of the material to transiently generate a temperature differential between the thin surface layer portion and a lower portion of the material sufficient to alter the thermal infrared emission spectrum of the material from the black-body thermal infrared emission spectrum of the material; and
   detecting the altered thermal infrared emission spectrum of the material while the altered thermal infrared emission spectrum is sufficiently free of self-absorption by the material of emitted infrared radiation, prior to the temperature differential propagating into the lower portion of the material to an extent such that the altered thermal infrared emission spectrum is no longer sufficiently free of self-absorption by the material of emitted infrared radiation, so that the detected altered thermal infrared emission spectrum is indicative of characteristics relating to molecular composition of the material.

2. A method according to claim I, wherein the step of cooling the surface layer portion of the material includes applying a cooling source to a part of the surface of the material to cause transient cooling of the thin surface layer portion and superposition of the transmission spectrum of the cooled layer on the emission of infrared radiation from the lower portion of the material below the cooled layer and being at a higher temperature than the cooled layer.

3. A method according to claim 2, wherein the step of cooling the thin surface layer portion includes applying a jet of cooling gas at a temperature lower than the temperature of the material being analyzed 4. A method according to claim 1, further comprising a step of determining characteristics relating to the molecular composition of the material in accordance with the detected altered thermal infrared emission.

5. A method according to claim 1, wherein the material is one of a solid material and a liquid material.

6. A method according to claim 5, wherein the solid material is one of a non-flexible material, a flexible material and a rubber-like material and the liquid material is a molten material.

7. A method according to claim 1, wherein the material is one of a stationary material and a moving material.

8. A method according to claim 7, wherein the step of detecting includes detecting the altered thermal infrared emission for a predetermined period of time upon cooling of the surface region.

9. A method according to claim 7, wherein the material is a moving material, the step of detecting includes setting the field of view of detection, and further comprising the step of moving the material into the field of view upon cooling of the surface of the material so as to enable detection of the altered thermal infrared emission, and then moving the material emitting the thermal altered infrared emission out of the field of view of detection.

10. A method according to claim 9, wherein the step of detecting includes utilizing a spectrometer and controlling the field of view thereof, and the step of moving includes utilizing conveyor means for transporting the material relative to the field of view of the spectrometer.

11. Apparatus for enabling analysis of a material comprising the steps of:
    means for cooling a thin surface layer portion of the material to transiently generate a temperature differential between the thin surface layer portion and a lower portion of the material sufficient to alter the thermal infrared emission spectrum of the material from the black-body thermal infrared emission spectrum of the material; and
    means for detecting the altered thermal infrared emission spectrum of the material while the altered thermal infrared emission spectrum is sufficiently free of self-absorption by the material of emitted infrared radiation, prior to the temperature differential propagating into the lower portion of the material to an extent such that the altered thermal infrared emission spectrum is no longer sufficiently free of self-absorption by the material of emitted infrared radiation, so that the detected altered thermal infrared emission spectrum is indicative of characteristics relating to molecular composition of the solid material.

12. Apparatus according to claim 11, wherein the means for cooling the surface layer of the material includes means for applying a cooling source to the surface of the material to cause transient cooling of the thin surface layer portion and superposition of the transmission spectrum of the cooled layer on the emission of infrared radiation from the lower portion of the material below the cooled layer and being at a higher temperature than the cooled layer.

13. Apparatus according to claim 12, wherein the means for cooling the thin surface layer portion includes means for applying a jet of cooling gas at a temperature lower than the temperature of the material being analyzed.

14. Apparatus according to claim 11, further comprising a means for determining characteristics relating to the molecular composition of the material in accordance with the detected altered thermal infrared emission.

15. Apparatus according to claim 11, wherein the material is one of a solid material and a liquid material.

16. Apparatus according to claim 15, wherein the solid material is one of a non-flexible material, a flexible material and a rubber-like material, and the liquid material is a molten material.

17. Apparatus according to claim 11, wherein the material is one of a stationary material and a moving material.

18. Apparatus according to claim 17, wherein the means for detecting includes control means for detecting the altered thermal infrared emission for a predetermined period of time upon cooling of the surface region.

19. Apparatus according to claim 17, wherein the material is a moving material, the means for detecting includes means for setting the field of view for detection, and further comprising means for moving the material into the field of view upon cooling of the surface of the material so as to enable detection of the altered thermal emission, the moving means moving the material emitting the altered infrared emission out of the field of view.

20. Apparatus according to claim 19, wherein the means for detecting includes a spectrometer having a field of view, and the moving means includes conveying means for transporting the material relative to the field of view of the spectrometer 21. Apparatus according to claim 20, wherein the spectrometer provides an output indicative of the detected altered thermal infrared emission, and further comprising means for processing the output of the spectrometer to determine characteristics relating to the molecular composition of the material.

* * * * *

UNITED STATES PATENT AND TRADEMARK OFFICE
CERTIFICATE OF CORRECTION

PATENT NO. : 5,070,242 Page 1 of 1
DATED : December 3, 1991
INVENTOR(S) : McClelland et al.

It is certified that error appears in the above-identified patent and that said Letters Patent is hereby corrected as shown below:

<u>Title page,</u>
Item [63], before CROSS REFERENCE TO RELATED APPLICATIONS, insert:
-- STATEMENT REGARDING FEDERALLY SPONSORED RESEARCH AND DEVELOPMENT This invention was made in part with Government support under the United States Department of Energy Contract No. W-7405-Eng-82. The Government may have certain rights in this invention. --

Signed and Sealed this

Twelfth Day of August, 2003

JAMES E. ROGAN
*Director of the United States Patent and Trademark Office*